US009766166B2

(12) United States Patent
Beebe et al.

(10) Patent No.: US 9,766,166 B2
(45) Date of Patent: *Sep. 19, 2017

(54) DEVICE AND METHOD INCORPORATING A SLIDEABLE LID FOR EXTRACTING A TARGETED FRACTION FROM A SAMPLE

(71) Applicant: Wisconsin Alumni Research Foundation, Madison, WI (US)

(72) Inventors: David J. Beebe, Monona, WI (US); Ben P. Casavant, Madison, WI (US); David J. Guckenberger, Oconomowoc, WI (US); Scott M. Berry, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 264 days.

This patent is subject to a terminal disclaimer.

(21) Appl. No.: 13/737,448

(22) Filed: Jan. 9, 2013

(65) Prior Publication Data

US 2014/0190894 A1  Jul. 10, 2014

(51) Int. Cl.
*G01N 1/34* (2006.01)
*B03C 1/00* (2006.01)
*C12N 15/10* (2006.01)
*B03C 1/02* (2006.01)
*B01L 3/00* (2006.01)

(52) U.S. Cl.
CPC .............. *G01N 1/34* (2013.01); *B01L 3/5088* (2013.01); *B01L 3/502761* (2013.01); *B01L 3/502792* (2013.01); *B03C 1/00* (2013.01); *B03C 1/02* (2013.01); *C12N 15/1006* (2013.01); *C12N 15/1013* (2013.01); *B01L 2200/0668* (2013.01); *B01L 2300/045* (2013.01); *B01L 2300/0803* (2013.01); *B01L 2300/0816* (2013.01); *B01L 2400/043* (2013.01); *B01L 2400/065* (2013.01); *B01L 2400/0644* (2013.01)

(58) Field of Classification Search
CPC  G01N 1/405; G01N 1/34; G01N 1/31; G01N 1/4077; G01N 33/48; G01N 33/538; G01N 33/543; B01D 21/00; B01D 2/00; B01D 11/0211; B01D 2221/10; B03C 1/02; B03C 1/01; B03C 5/00; B03C 5/02; B03C 1/00; B03C 2201/18; C07K 1/14; C07K 1/24–1/28; C07H 21/00; C07H 1/06; B01L 2400/043
USPC ........ 422/500, 501, 527, 503; 204/545, 557, 204/554, 560, 660; 536/25.4, 23.1; 530/350, 412; 436/177; 435/283.1, 435/308.1; 210/695, 222
See application file for complete search history.

(56) References Cited

U.S. PATENT DOCUMENTS

| | | | |
|---|---|---|---|
| 5,279,936 A | 1/1994 | Vorpahl | |
| 6,117,398 A | 9/2000 | Bienhaus et al. | |
| 6,312,910 B1 | 11/2001 | Vellinger et al. | |
| 7,820,454 B2 | 10/2010 | Su et al. | |
| 8,017,340 B2 | 9/2011 | Collier et al. | |
| 8,048,633 B2 | 11/2011 | Collier et al. | |
| 8,304,188 B2 | 11/2012 | Kelso et al. | |
| 2002/0150683 A1* | 10/2002 | Troian ............... | B01F 13/0071 137/828 |
| 2004/0136875 A1* | 7/2004 | Seul .................... | B01J 19/0046 436/518 |
| 2004/0224380 A1 | 11/2004 | Chou et al. | |
| 2005/0112601 A1 | 5/2005 | Hassibi et al. | |
| 2005/0208548 A1 | 9/2005 | Block et al. | |
| 2005/0227349 A1 | 10/2005 | Kim et al. | |
| 2006/0024824 A1 | 2/2006 | Woodside et al. | |
| 2006/0118494 A1* | 6/2006 | Rundt .................... | B03C 1/284 210/695 |
| 2007/0042396 A1 | 2/2007 | Park et al. | |
| 2008/0124779 A1 | 5/2008 | Oh et al. | |
| 2008/0226500 A1 | 9/2008 | Shikida et al. | |
| 2008/0233630 A1 | 9/2008 | Kim et al. | |
| 2009/0191594 A1 | 7/2009 | Ohashi | |
| 2009/0197329 A1 | 8/2009 | Lee et al. | |

(Continued)

FOREIGN PATENT DOCUMENTS

WO  2006071770  7/2006

OTHER PUBLICATIONS

Berry et al., "One-step purification of nucleic acid for gene expression analysis via immiscible filtration assisted by surface tension (IFAST)", Lab on a Chip, vol. 11, No. 10, pp. 1747-1753 (2011).
Strotman et al., "Facile and rapid DNA extraction and purification from food matrices using IFAST (immiscible filtration assisted by surface tension)", Analyst, vol. 137, No. 17, pp. 4023-4028 (2012).
Berry et al., "Streamlining immunoassays with immiscible filtrations assisted by surface tension", Analytical Chemistry, vol. 84, No. 13, pp. 5518-5523 (2012).

(Continued)

*Primary Examiner* — Jennifer Pitrak McDonald
*Assistant Examiner* — Qing Xu
(74) *Attorney, Agent, or Firm* — Boyle Fredrickson, S.C.

(57) ABSTRACT

A device and a method for isolating a target from a biological sample are provided. The target is bound to solid phase substrate to form target bound solid phase substrate. The device includes a lower plate with an upper surface having a plurality of regions. The biological sample is receivable on a first of the regions. An upper plate has a lower surface directed to the upper surface of the lower plate. A force is positioned adjacent the upper plate and attracts the target bound solid phase substrate toward the lower surface of the upper plate. At least one of the upper plate and the lower plate is movable from a first position wherein the target bound solid phase substrate in the biological sample are drawn to the lower surface of the upper plate and a second position wherein the target bound solid phase substrate are isolated from the biological sample.

7 Claims, 6 Drawing Sheets

(56) References Cited

U.S. PATENT DOCUMENTS

| | | |
|---|---|---|
| 2009/0246782 A1 | 10/2009 | Kelso et al. |
| 2010/0273142 A1 | 10/2010 | Prins et al. |
| 2010/0291666 A1 | 11/2010 | Collier et al. |
| 2011/0213133 A1* | 9/2011 | Beebe et al. ............... 530/412 |
| 2012/0028342 A1 | 2/2012 | Ismagilov et al. |
| 2012/0094275 A1 | 4/2012 | Rao et al. |

OTHER PUBLICATIONS

Sur et al, "Immiscible phase nucleic acid purification eliminates PCR inhibitors with a single pass of paramagnetic particles through a hydrophobic liquid", The Journal of Molecular Diagnostics, vol. 12, No. 5, pp. 620-628 (2010).
Kim et al., "Removal of malaria-infected red blood cells using magnetic cell separators: A computational study", Applied Mathematics and Computation, vol. 218, No. 12, pp. 6841-6850 (2012).
U.S. Appl. No. 60/638,177, filed Dec. 21, 2005, Collier et al.
"Development of an enzymatic reaction device using magnetic bead-cluster handling", Shikida et al, J. Micromech. Microeng. 16 (2006) 1875-1883.
"Controlled microfluidic interfaces", Atencia et al, Nature, vol. 437, Sep. 29, 2005, 648-655.
"Using wettability and interfacial tension to handle droplets of magnetic beads in a micro-chemical-analysis system", Shikida et al, Sensors and Actuators B 113 (2006) 563-569.
"Droplet-based gene expression analysis using a device with magnetic force-based-droplet-handling system", Okochi et al, Journal of Bioscience and Bioengineering, vol. 109, No. 2, 2010, 193-197.
"On-chip polymerase chain reaction microdevice employing a magnetic droplet-manipulation system", Tsuchiya et al, Sensors and Actuators B 130 (2008) 583-588.
"A novel Real Time micro PCR based Point-of-Care device for *Salmonella* detection in human clinical samples", Verdoy et al, Biosensors and Bioelectronics 332 (2012) 259-265.
"Forced motion of a probe particle near the colloidal glass transition", Habdas et al, Europhys. Lett., 67(3), pp. 477-583 (2004).
"Development of a Low-Resource RNA Extraction Cassette Based on Surface Tension Valves", Bordelon et al, Appl. Mater. Interfaces 2011, 3, 2161-2168.
EP Appln. No. 13870990.2, Supplementary European Search Report dated Jul. 4, 2016, 8 pages.

* cited by examiner

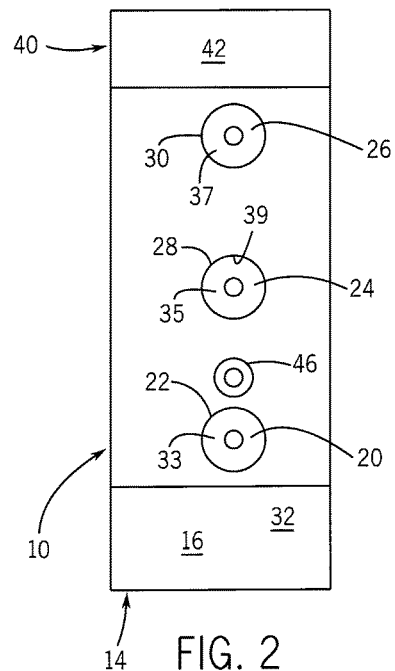
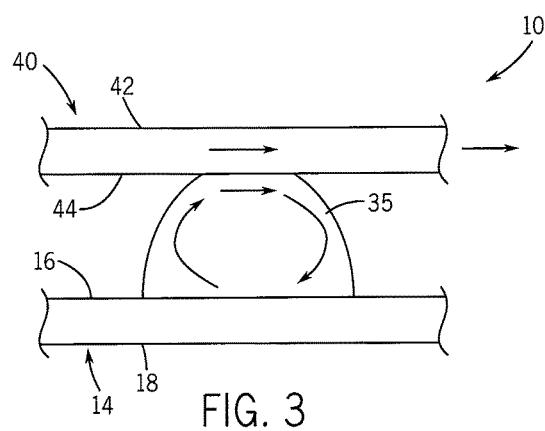

US 9,766,166 B2

DEVICE AND METHOD INCORPORATING A SLIDEABLE LID FOR EXTRACTING A TARGETED FRACTION FROM A SAMPLE

REFERENCE TO GOVERNMENT GRANT

This invention was made with government support under W81XWH-9-1-0192 awarded by the ARMY/MRMC. The government has certain rights in the invention.

FIELD OF THE INVENTION

The present invention relates generally to the preparation of biological samples, and in particular, to a device for and a method of extracting a targeted fraction from a biological sample.

BACKGROUND AND SUMMARY OF THE INVENTION

Methods for isolating DNA, RNA, and proteins from complex biological samples are some of the most crucial steps in molecular biology. However, these methods are often overlooked within the biological sample processing workflow. As the throughput of downstream analytical techniques have increased, sample preparation methods have become a limiting factor in overall throughput. Many of the most used methods for sample preparation are very time consuming and can involve many steps including substrate binding, multiple wash steps, dilutions, or other processes that can result in loss of sample or dramatic increases in assay time.

The ability to use functionalized paramagnetic particles (PMPs) to isolate analyte of interest has expanded the utility of isolation methods across a range of platforms. One of PMPs advantages is that the particles are flexible for use in many system configurations since only a magnet is required for actuation and analyte isolation. The ways to isolate an analyte of interest from a given sample can further divided into two basic methods. First, in the current primary method for using PMPs, the PMPs are held stationary while fluid is washed over the substrate to remove the background sample and any contaminants. Limitations of this popular method include the loss of the original input sample, allowing only a single effective isolation per sample, and the inefficiency of dilution-based sample preparation techniques, thereby necessitating multiple washes to effectively remove contaminants and leading to lengthy workflows. Second, recent work has demonstrated the ability to remove the PMPs from the original sample of interest using exclusion-based methods. These methods generally leverage gravitational forces or the dominance of surface tension at the microscale to position original samples and physically drag the PMPs out of the input sample along the surface of a device through some immiscible phase (e.g., air or oil) and into a second aqueous phase. These methods have been highly effective at isolating analyte with high specificity and selectivity. Further, these methods have been beneficial for their elegant workflow since isolation can be performed in a matter of seconds. Though effective, problems for these methods exist in the need for an immiscible fluid (oil) that can complicate both the fabrication and use of these techniques on larger scales and the function of 'dragging' particles along a surface resulting in a friction-based loss of sample.

Therefore, it is a primary object and feature of the present invention to provide a device for and a method of extracting a targeted fraction from a biological sample.

It is a further object and feature of the present invention to provide a device for and a method of extracting a targeted fraction from a biological sample that is simple to fabricate and implement.

It is a still further object and feature of the present invention to provide a device for and a method of extracting a targeted fraction from a biological sample that reduces friction-based losses of the targeted fraction of prior devices/methods.

In accordance with the present invention, a device is provided for isolating a target from a biological sample. The target is bound to solid phase substrate to form target bound solid phase substrate. The device includes a lower plate with an upper surface having a plurality of regions. The biological sample is receivable on a first of the regions. An upper plate has a lower surface directed to the upper surface of the lower plate. A force adjacent the upper plate attracts the target bound solid phase substrate toward the lower surface of the upper plate. At least one of the upper plate and the lower plate is movable from a first position wherein the target bound solid phase substrate in the biological sample are drawn to the lower surface of the upper plate and a second position wherein the target bound solid phase substrate are isolated from the biological sample.

The regions of the lower plate are hydrophilic and the portions of the upper surface of the outside of the regions of the lower plate are hydrophobic. The lower surface of the upper plate is also hydrophobic. The upper plate is axially movable between the first and second positions or is rotatably between the first and second positions. The upper surface of the lower plate and lower surface of the upper surface are spaced by a predetermined distance.

In accordance with a further aspect of the present invention, a method is provided for isolating a target from a biological sample. The target is bound to solid phase substrate to form target bound solid phase substrate. The method includes the steps of providing the biological sample at a region of a surface of a lower plate and positioning an upper plate in spaced relation to the lower plate. The upper plate has a lower surface directed to the upper surface of the lower plate. The target bound solid phase substrate are drawn toward the lower surface of the upper plate with a force. At least one of the lower plate and the upper plate is moved from a first position wherein the target bound solid phase substrate in the biological sample are drawn toward the lower surface of the upper plate to a second position wherein the target bound solid phase substrate are isolated from the biological sample.

The upper surface of the lower plate may include a plurality of regions that are hydrophilic. The upper surface of the lower surface outside of the regions are hydrophobic. The lower surface of the upper plate is hydrophobic. The upper plate moves along a longitudinal axis between the first and second positions or is rotatable between the first and second positions. It is contemplated to space the upper surface of the lower plate and lower surface of the upper surface by a predetermined distance.

In accordance with a still further aspect of the present invention, a method is provided for isolating a target from a biological sample. The target is bound to solid phase substrate to form target bound solid phase substrate. The method includes the step of providing the biological sample at a first region of a surface of a first plate. A fluid is deposited on a second region of the surface of the first plate. A second plate is positioned in spaced relation to the first plate. The second plate has a hydrophobic surface directed towards the surface of the first plate. The target bound solid phase substrate are drawn toward the surface of the second plate with a force. At least one of the first plate and the second plate is moved from a first position wherein the target bound solid phase substrate in the biological sample are drawn toward the surface of the second plate to a second position wherein the target bound solid phase substrate are isolated from the biological sample.

The portions of the surface of the first plate outside of the first and second regions are hydrophobic. The second plate moves along a longitudinal axis between the first and second positions or is rotatable between the first and second positions. The surface of the second plate is spaced from the surface of the first plate by a predetermined distance. It is intended for the force to be magnetic and for the target bound solid phase substrate to be received in the fluid with the at least one of the first plate and the second plate in the second position. The method may also include the step of isolating the target bound solid phase substrate from the force.

BRIEF DESCRIPTION OF THE DRAWINGS

The drawings furnished herewith illustrate a preferred construction of the present invention in which the above advantages and features are clearly disclosed as well as others which will be readily understood from the following description of the illustrated embodiment.

In the drawings:

FIG. 2 is a top plan view of the device of the present invention in the third configuration;

FIG. 3 is an enlarged, cross-sectional view showing a portion of the device of the present invention during operation;

DETAILED DESCRIPTION OF THE DRAWINGS

Figure 1A:
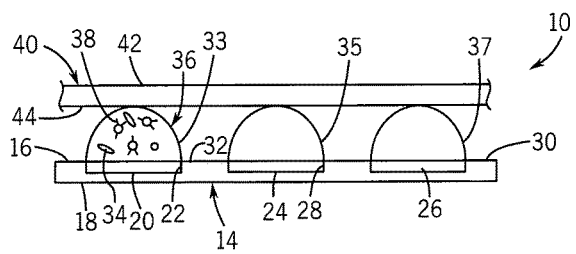
FIG. 1A is a cross-sectional view of a device in accordance with the present invention in an initial configuration.

Referring to FIGS. 1-3, a device and a method for extracting and purifying a targeted fraction, such as DNA, RNA, and proteins, from complex biological samples, including cultured cells, tissue samples and other biological materials, in accordance with the present invention is generally designated by the reference numeral 10. Device 10 includes a lower first plate 14 having upper and lower surfaces 16 and 18, respectively. Except as hereinafter described, upper surface 16 of lower plate 14 is hydrophobic. Upper surface 16 of first plate 14 includes first region 20 defined by edge 22 such that first region 20 has a generally circular configuration. However, other configurations are contemplated as being within the scope of the present invention. It is intended for first region 20 to spatially retain a selected fluid thereon, as hereinafter described. By way of example, it is contemplated for first region 20 to be hydrophilic. Alternatively, it can be appreciated that first region 20 may: 1) utilize various geometric configurations; 2) take the form of a well within upper surface 16 of first plate 14; or 3) include a wall extending around the periphery thereof to spatially retain a selected fluid thereon.

Upper surface 16 of first plate 14 may further include second and third regions 24 and 26, respectively, defined by corresponding edges 28 and 30, respectively, such that second and third regions 24 and 26, respectively, have generally circular configurations. However, other configurations are contemplated as being within the scope of the present invention. It is intended for second and third regions 24 and 26, respectively, to spatially retain selected fluids thereon, as hereinafter described. By way of example, it is contemplated for second and third regions 24 and 26, respectively, to be hydrophilic. Alternatively, it can be appreciated that second and third regions 24 and 26, respectively, may: 1) utilize various geometric configurations; 2) take the form of wells within upper surface 16 of first plate 14; or 3) include walls extending around the peripheries thereof to spatially retain selected fluids thereon. Further, the portion of upper surface 16 of first plate 14 outside of first, second and third regions 20, 24 and 26, respectively, defines hydrophobic region 32.

Device 10 further includes an upper second plate 40 having upper and lower surfaces 42 and 44, respectively. Except as hereinafter described, lower surface 44 of second plate 40 is hydrophobic. Magnet 46 is supported by upper surface 42 of second plate 40. It is contemplated for magnet 46 to be axially movable between a first position wherein magnet 46 is adjacent to upper surface 42 of second plate 40 and a second position axially spaced from upper surface 42 of second plate 40, for reasons hereinafter described.

It is intended to utilize device 10 to extract a targeted fraction, such as DNA, RNA, proteins nucleic acids, whole cells and/or the like, from biological sample 36. As is known, biological sample 36 may include non-desired material 38 such as lysate, bodily fluids, forensic samples, and/or biological contaminations. In order to prepare biological sample 36 for extraction of the fraction, an appropriate reagent is added to biological sample 36 and mixed such that the fraction binds to a solid phase substrate in the reagent to form fraction-bound solid phase substrate 38. It is contemplated for the solid phase substrate to be attracted to a corresponding force. For example, the solid phase substrate may be a paramagnetic material attracted to a corresponding magnetic field. Other non-magnetic mechanisms such as gravity, optical force, ultrasonic actuation or the like are contemplated as being within the scope of the present invention.

Once mixed with the reagent, droplet 33 of biological sample 36 is deposited on first region 20 in any conventional matter such as by a micropipette or like. Alternatively, it is contemplated to provide a channel within first plate 14 having an output in communication with first region 20 so as to allow biological sample 36 to be flowed in first region 20. In addition, droplet 35 of a first reagent (e.g. wash, secondary antibody, etc.) is deposited on second region 24 and droplet 37 of a second reagent is deposited on third region 26. It is contemplated for the volumes of droplets 33, 35 and 37 to be generally equal. It can be appreciated that the hydrophillic nature of first, second and third regions 20, 24 and 26, respectively, act to pin droplets 33, 35 and 37 thereon. In addition, the hydrophobic region 32 of upper surface 16 of first plate 14 further acts to retain droplets 33, 35 and 37 on first, second and third regions 20, 24 and 26, respectively.

After depositing droplets 33, 35 and 37 on first, second and third regions 20, 24 and 26, respectively, second plate 40 is positioned such that lower surface 44 thereof is in close proximity to or makes contact with droplets 33, 35 and 37 and such that magnet 46 is axially aligned with first region 20 of upper surface 16 of first plate 14, FIG. 1A. Lower surface 44 of second plate 40 is maintained a predetermined distance from upper surface 16 of first plate 14 such that droplets 33, 35 and 37 maintain their generally cylindrical shapes and are not squashed.

Figure 1B:
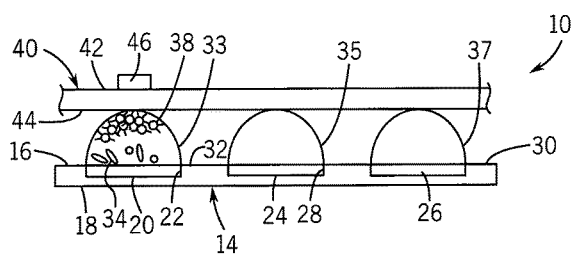
FIG. 1B is a cross-sectional view of the device of the present invention in a second configuration.
Figure 1C:
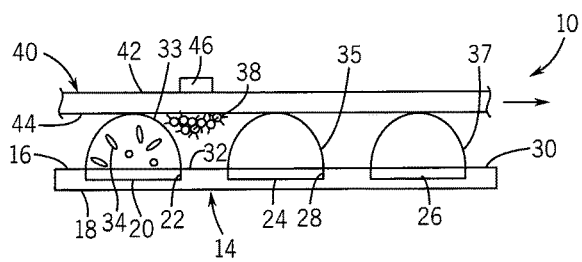
FIG. 1C is a cross-sectional view of the device of the present invention in a third configuration.
Figure 1D:
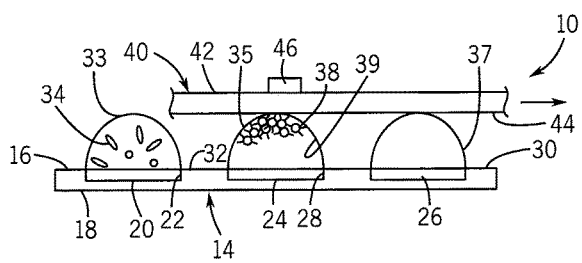
FIG. 1D is an isometric view of a device of the present invention in a fourth configuration.
Figure 1E:
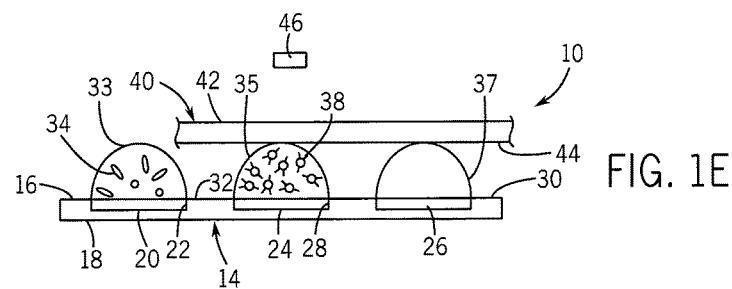
FIG. 1E is a cross-sectional view of the device of the present invention in a fifth configuration.
Figure 1F:
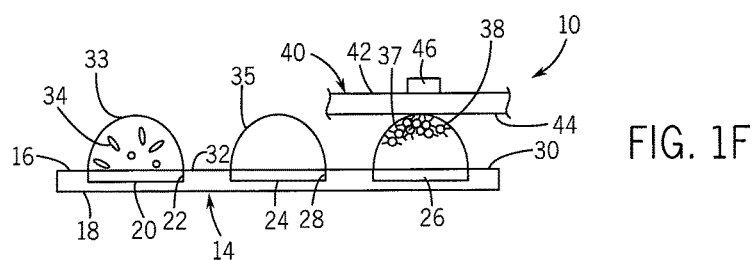
FIG. 1F is a cross-sectional view of the device of the present invention in a sixth configuration.
Figure 1G:
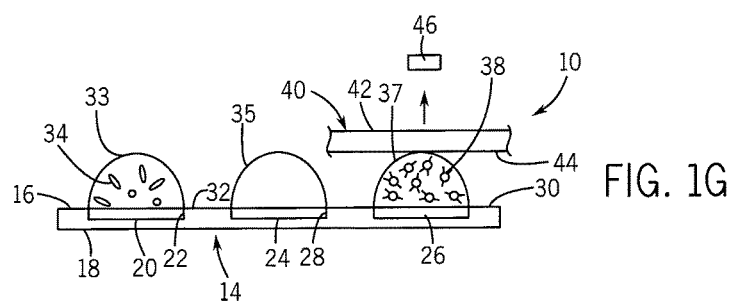
FIG. 1G is a cross-sectional view of the device of the present invention in a sixth configuration.

With second plate 40 positioned, as heretofore described, magnet 46 is positioned adjacent upper surface 42 of second plate 40 and magnetically attracts fraction-bound solid phase substrate 38 such that fraction-bound solid phase substrate 38 are drawn toward lower surface 44 of second plate 40, FIG. 1B. Any undesired (or unbound) material in droplet 33 is free to drop towards upper surface 16 of first plate 14. Thereafter, with first plate 14 remaining stationary, second plate 40 is moved axially in a first direction, FIG. 1C. The hydrophobic nature of lower surface 44 of second plate 40 prevents second plate 40 from adhering to droplets 33, 35 and 37, thereby insuring that droplets 33, 35 and 37 maintain their integrity as second plate 40 is axially moved. As second plate 40 is moved, magnet 46 retains fraction-bound solid phase substrate 38 against lower surface 44 of second plate 40, thereby allowing fraction-bound solid phase substrate 38 to break the surface tension of droplet 33 when fraction-bound solid phase substrate 38 reach the outer periphery thereof. Second plate 40 continues to be moved in the first direction such that magnet 46 is axially aligned with second region 24 of upper surface 16 of first plate 14, FIG. 1D. Fraction-bound solid phase substrate 38 may be deposited in droplet 35 on second region 24 simply by moving magnet 46 axially away from upper surface 42 of second plate 40, FIG. 1E, thereby freeing fraction-bound solid phase substrate 38 from the magnetic force thereof. To assure that all of fraction-bound solid phase substrate 38 are retained in droplet 35, first plate 14, and hence magnet 46, is slid past droplet 35 prior to axially moving magnet 46 away from upper surface 42 of second plate 40. More specifically, the movement of first plate 14 and second plate 40 with respect to each other causes Couette flow within droplet 35 such that droplet 35 mixes within itself, FIG. 3. In addition, the surface tension of posterior end 39 of droplet 35 pulls fraction-bound solid phase substrate 38 off hydrophobic, lower surface 44 of second plate 40.

In order to move fraction-bound solid phase substrate 38 into droplet 37, magnet 46 is repositioned adjacent of upper surface 42 of second plate 40 in axial alignment with second region 24 of upper surface 16 of first plate 14. With magnet 46 repositioned, as heretofore described, magnet 46 magnetically attracts fraction-bound solid phase substrate 38 such that fraction-bound solid phase substrate 38 are drawn toward lower surface 44 of second plate 40, FIG. 1D. With first plate 14 remaining stationary, second plate 40 is moved axially in the first direction. As second plate 40 is moved, magnet 46 retains fraction-bound solid phase substrate 38 against lower surface 44 of second plate 40, thereby allowing fraction-bound solid phase substrate 38 to break the surface tension of droplet 35 when fraction-bound solid phase substrate 38 reach the outer periphery thereof. Second plate 40 continues to be moved in the first direction such that magnet 46 is axially aligned with third region 26 of upper surface 16 of first plate 14, FIG. 1F. With magnet 46 is axially aligned with third region 26 of upper surface 16 of first plate 14, magnet 46 is moved axially away from upper surface 42 of second plate 40, FIG. 1G, thereby freeing fraction-bound solid phase substrate 38 within droplet 37 on third region 26. As described, fraction-bound solid phase substrate 38 is then allowed to passively mix into droplet 37. To assure that all of fraction-bound solid phase substrate 38 beads are retained in droplet 37, first plate 14, and hence magnet 46, is slid past droplet 37 prior to axially moving magnet 46 away from upper surface 42 of second plate 40. More specifically, the movement of first plate 14 and second plate 40 with respect to each other causes Couette flow within droplet 37 such that droplet 37 mixes within itself. In addition, the surface tension of the posterior end of droplet 37 pulls fraction-bound solid phase substrate 38 off hydrophobic, lower surface 44 of second plate 40.

It can be appreciated that the above description of device 10 is merely exemplary of the present invention. Various modifications to device 10 are possible without deviating from the scope of the present invention. By way of example, it is contemplated for first plate 14 to be axially moveable with respect to second plate 40, such movement of first plate 14 (or a combination of movement of first and second plates 14 and 40, respectively) results in the droplets 33, 35 and 37 aligning with magnet 46, for reasons heretofore described. It is further contemplated to provide additional (or fewer) hydrophilic regions on upper surface 16 of first plate 14 so as to allow a user to effectuate additional (or fewer) processing steps on fraction-bound solid phase substrate 38, e.g. additional washings of fraction-bound solid phase substrate 38. Further, upper surface 16 of first plate 14 may include an array of hydrophilic regions and a corresponding array of magnets may be supported on second plate 40. As a result, a plurality of extraction operations in accordance with the methodology of the present invention may be simultaneously conducted utilizing a single device 10. In such an arrangement, it is contemplated to provided a wall or fence about each "set" of hydrophilic regions so as to effectively isolate each "set" of hydrophilic regions from the other sets in the array, thereby preventing potential cross contamination between the sets. In an alternate embodiment, it is contemplated to permanently affix magnet 46 to second plate 40. As such, instead of axially moving magnet 46 away from upper surface 42 of second plate 40 to release fraction-bound solid phase substrate 38 into a corresponding droplet, second plate 40 may be simply removed from contact with the droplets. With second plate 40 disengaged from the droplets, fraction-bound solid phase substrate 38 is allowed to passively mix in the desired droplet. It is noted that since lower surface 44 of second plate 40 is hydrophobic, the droplets do not adhere thereto thereby allowing the droplets to maintain their integrity.

Referring to FIGS. 4-7, an alternate embodiment of a device in accordance with the present invention is generally designated by the reference numeral 60. Device 60 includes lower first plate 72 having upper and lower surfaces 74 and 76, respectively. First plate 72 has a center, a diameter and a generally circular configuration defined by outer edge 78. Support 79 extends axially away from center of first plate 72 for rotationally supporting second plate 104 thereon. Except as hereinafter described, upper surface 74 of first plate 72 is hydrophobic. Upper surface 74 of first plate 72 includes a first region 80 defined by edge 82 such that first region 80 has a generally circular configuration. The center of first region 80 is a predetermined radial distance from center 88 of first plate 72. It is intended for first region 80 to spatially retain a selected fluid thereon, as hereinafter described. By way of example, it is contemplated for first region 80 to be hydrophilic. Alternatively, it can be appreciated that first region 80 may: 1) utilize various geometric configurations; 2) take the form of a well within upper surface 74 of first plate 72; or 3) include a wall extending around the periphery thereof to spatially retain a selected fluid thereon.

Upper surface 74 of first plate 72 may further include second and third regions 90 and 92, respectively, defined by corresponding edges 94 and 96, respectively, such that second and third regions 90 and 92, respectively, have generally circular configurations. The centers of second and third regions 90 and 92, respectively, are spaced from center 88 of first plate 72 by the predetermined radial distance. It is intended for second and third regions 90 and 92, respectively, to spatially retain selected fluids thereon, as hereinafter described. By way of example, it is contemplated for second and third regions 90 and 92, respectively, to be hydrophilic. Alternatively, it can be appreciated that second and third regions 90 and 92, respectively, may: 1) utilize various geometric configurations; 2) take the form of wells within upper surface 74 of first plate 72; or 3) include walls extending around the peripheries thereof to spatially retain selected fluids thereon. The portion of upper surface 74 of first plate 72 outside of first, second and third regions 80, 90 and 92, respectively, defines hydrophobic region 102.

Second plate 104 has a center, a diameter generally equal to the diameter of first plate 72, and upper and lower surfaces 106 and 108, respectively. Upper second plate 104 is rotatably supported by support 79 in spaced relation to first plate 72 such that the center of second plate 104 is axially aligned with the center of first plate 72. Lower surface 108 of second plate 104 is hydrophobic. Magnet 110 is supported by upper surface 106 of second plate 104 at a location radially spaced from the center of second plate by the predetermined radial distance. Magnet 110 is axially movable between a first position wherein magnet 110 is adjacent to upper surface 106 of second plate 104 and a second position axially spaced from upper surface 106 of second plate 104, for reasons hereinafter described.

Figure 4:
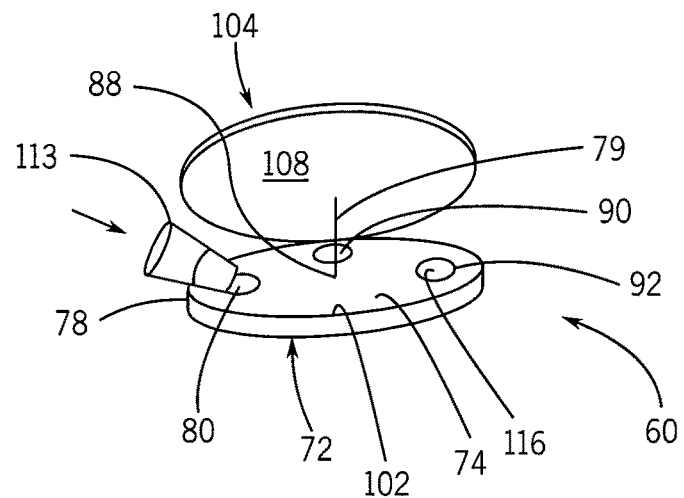
FIG. 4 is an isometric view of an alternate embodiment of a device in accordance with the present invention in an initial configuration.
Figure 5:
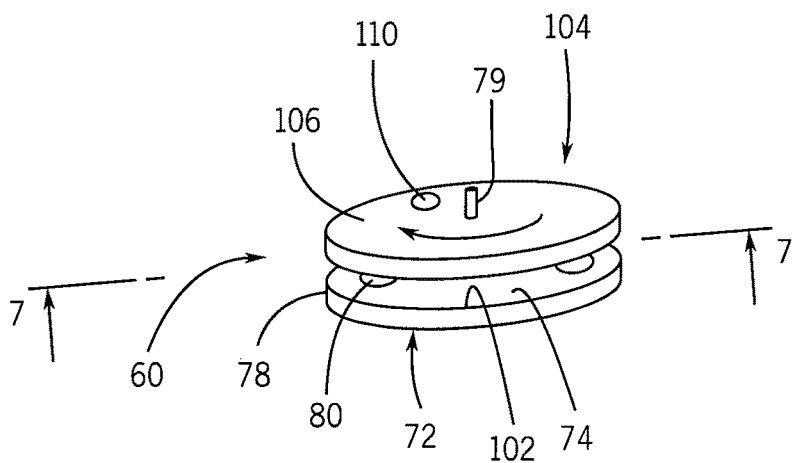
FIG. 5 is an isometric view of the device of FIG. 4 in second configuration.
Figure 6:
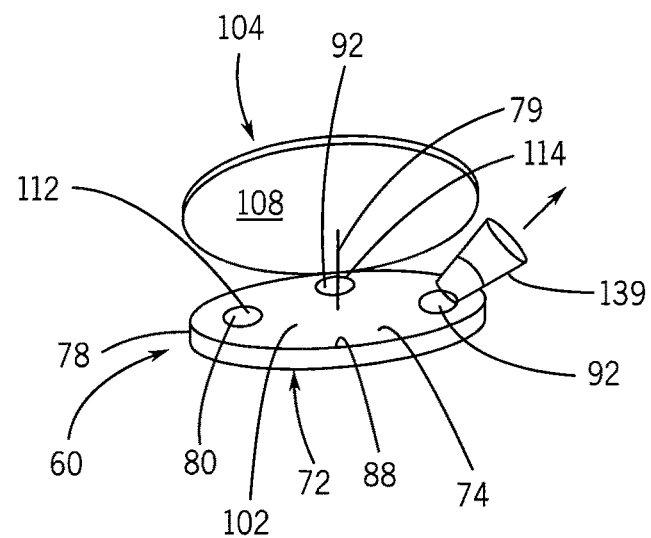
FIG. 6 is an isometric view of the device of FIG. 4 in third configuration.
Figure 7:
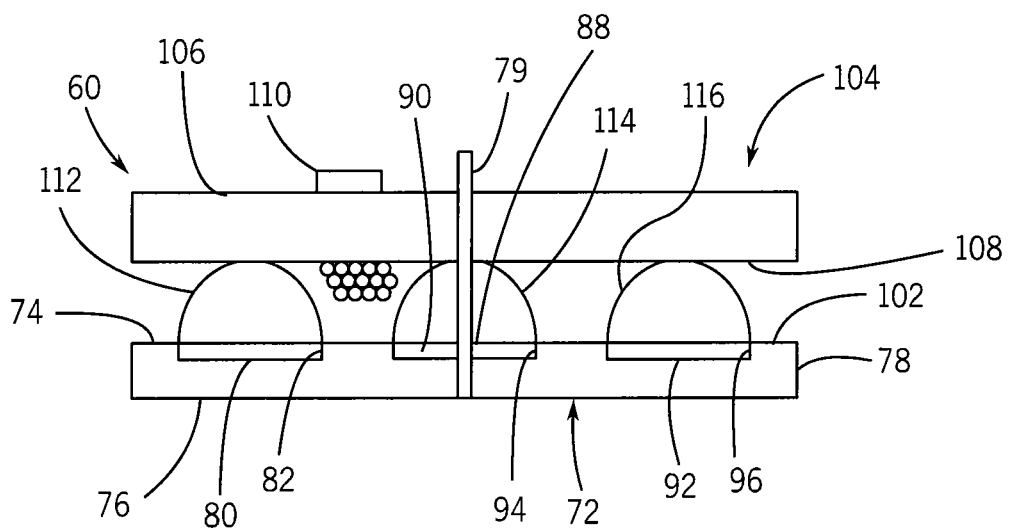
FIG. 7 is a cross-sectional view of the device of FIG. 5 taken along line 7-7.

In order to extract the targeted fraction from biological sample 36, droplet 112 of biological sample 36 is deposited on first region 80 in any conventional matter such as by a micropipette 113 or like, FIG. 4. Alternatively, it is contemplated to provide a channel within first plate 72 having an output in communication with first region 80 so as to allow biological sample 36 to be flowed in first region 80. In addition, droplet 114 of a first reagent (e.g. wash, secondary antibody, etc.) is deposited on second region 90 and droplet 116 of a second reagent is deposited on third region 92. It is contemplated for the volumes of droplets 112, 114 and 116 to be generally equal. Second plate 104 is positioned such that lower surface 108 thereof is in close proximity to or makes contact with droplets 112, 114 and 116 and such that magnet 110 is axially aligned with first region 80 of upper surface 74 of first plate 72. Lower surface 108 of second plate 104 is maintained a predetermined distance from upper surface 74 of first plate 72 by support 79 such that droplets 112, 114 and 116 maintain their generally cylindrical shapes and are not squashed.

With second plate 104 positioned as heretofore described, magnet 110 magnetically attracts fraction-bound solid phase substrate 38 such that fraction-bound solid phase substrate 38 are drawn toward lower surface 108 of second plate 104. With first plate 72 remaining stationary, second plate 104 is rotated axially in a first direction, FIGS. 5 and 7. As second plate 104 is moved, magnet 110 retains fraction-bound solid phase substrate 38 against lower surface 108 of second plate 104, thereby allowing fraction-bound solid phase substrate 38 to break the surface tension of droplet 112 when fraction-bound solid phase substrate 38 reach the outer periphery thereof. Second plate 104 continues to be moved in the first direction such that magnet 110 is axially aligned with second region 90 of upper surface 74 of first plate 72. Fraction-bound solid phase substrate 38 may be deposited in droplet 114 on second region 90 simply by moving magnet 110 axially away from upper surface 74 of second plate 104. To assure that all of fraction-bound solid phase substrate 38 are retained in droplet 114, second plate 104, and hence magnet 110, is slid past droplet 114 prior to axially moving magnet 110 away from upper surface 106 of second plate 104. More specifically, the movement of first plate 72 and second plate 104 with respect to each other causes Couette flow within droplet 114 such that droplet 114 mixes within itself. In addition, the surface tension of the posterior end of droplet 114 pulls fraction-bound solid phase substrate 38 off hydrophobic, lower surface 108 of second plate 104.

In order to move fraction-bound solid phase substrate 38 into droplet 116, magnet 110 is repositioned adjacent of upper surface 106 of second plate 104 in axial alignment with second region 90 of upper surface 74 of first plate 72. With magnet 110 repositioned, as heretofore described, magnet 110 magnetically attracts fraction-bound solid phase substrate 38 such that fraction-bound solid phase substrate 38 are drawn toward lower surface 108 of second plate 104. With first plate 72 remaining stationary, second plate 104 is rotated in the first direction. As second plate 104 is moved, magnet 110 retains fraction-bound solid phase substrate 38 against lower surface 108 of second plate 104, thereby allowing fraction-bound solid phase substrate 38 to break the surface tension of droplet 114 when fraction-bound solid phase substrate 38 reach the outer periphery thereof. Second plate 104 continues to be rotated in the first direction such that magnet 110 is axially aligned with third region 92 of upper surface 74 of first plate 72. With magnet 110 is axially aligned with third region 92 of upper surface 106 of first plate 104, magnet 110 is moved axially away from upper surface 106 of second plate 104, thereby depositing fraction-bound solid phase substrate 38 in droplet 116 on third region 92. As described, fraction-bound solid phase substrate 38 is then allowed to passively mix into droplet 116. Droplet 116 may be removed, such as by micropipette 139, FIG. 6, for further processing.

It can be appreciated that the above description of device 60 is merely exemplary of the present invention. Various modifications to device 60 are possible without deviating from the scope of the present invention. By way of example, it is contemplated for first plate 72 to be moveable with respect to second plate 104, such movement of first plate 72 (or a combination of movement of first and second plates 72 and 104, respectively) results in the droplets 112, 114 and 116 aligning with magnet 46, for reasons heretofore described. It is further contemplated to provide additional (or fewer) hydrophilic regions on upper surface 74 of first plate 72 so as to allow a user to effectuate additional (or fewer) processing steps on fraction-bound solid phase substrate 38, e.g. additional washings of fraction-bound solid phase substrate 38. Further, upper surface 74 of first plate 72 may include an array of hydrophilic regions circumferentially spaced thereon and a corresponding array of magnets supported second plate 104. As a result, a plurality of extraction operations in accordance with the methodology of the present invention may be simultaneously conducted utilizing a single device 60. In such an arrangement, it is contemplated to provided a wall or fence about each "set" of hydrophilic regions so as to effectively isolate each "set" of hydrophilic regions from the other sets in the array, thereby preventing potential cross contamination between the sets. In an alternate embodiment, it is contemplated to permanently affix magnet 110 to second plate 104. As such, instead of axially moving magnet 110 away from upper surface 106 of second plate 104 to release fraction-bound solid phase substrate 38 into a corresponding droplet, second plate 104 is simply removed from contact with the droplets. With second plate 104 disengaged from the droplets, fraction-bound solid phase substrate 38 is allowed to passively mix into the desired droplet. It is noted that since lower surface 108 of second plate 104 is hydrophobic, the droplets do not adhere thereto thereby allowing the droplets to maintain their integrity.

Figure 8:
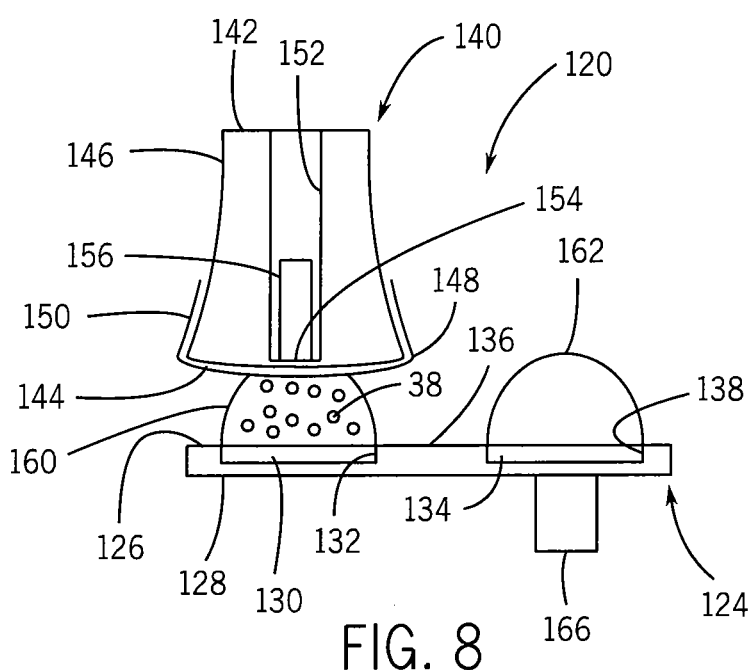
FIG. 8 is a cross-sectional view of a still further embodiment of a device in accordance with the present invention in an initial configuration.
Figure 9:
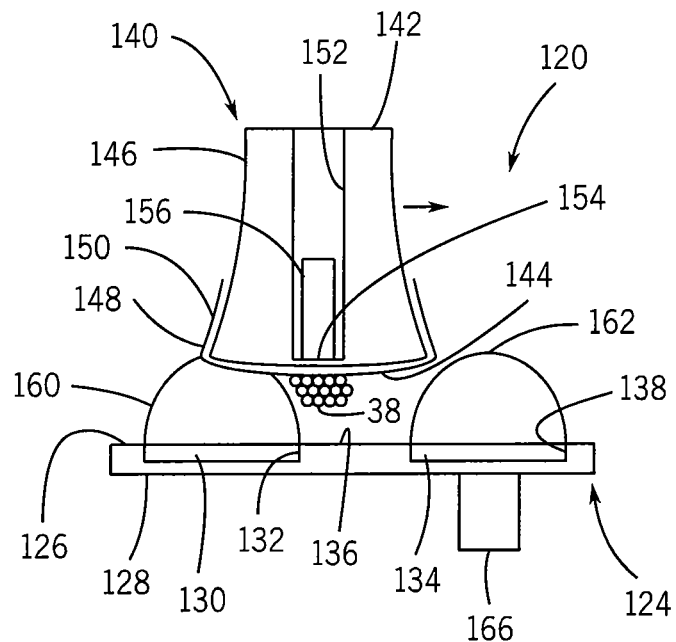
FIG. 9 is a cross-sectional view of a device in accordance with the present invention in a second configuration.
Figure 10:
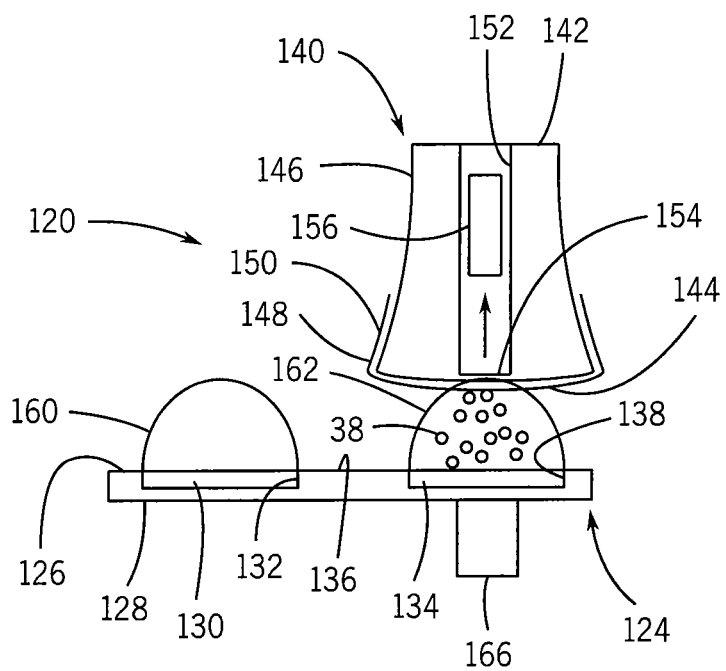
FIG. 10 is a cross-sectional view of a device in accordance with the present invention in a third configuration.

Referring to FIGS. 8-10, a still further embodiment of a device in accordance with the present invention is generally designated by the reference number 120. Device 120 includes a lower first plate 124 having upper and lower surfaces 126 and 128, respectively. Except as hereinafter described, upper surface 126 of lower plate 124 is hydrophobic. Upper surface 126 of first plate 124 includes first region 130 defined by edge 132 such that first region 130 has a generally circular configuration. However, other configurations are contemplated as being within the scope of the present invention. It is intended for first region 130 to spatially retain a selected fluid thereon, as hereinafter described. By way of example, it is contemplated for first region 130 to be hydrophilic. Alternatively, it can be appreciated that first region 130 may: 1) utilize various geometric configurations; 2) take the form of a well within upper surface 126 of first plate 124; or 3) include a wall extending around the periphery thereof to spatially retain the selected fluid thereon.

Upper surface 126 of first plate 124 may further include second region 134 defined by corresponding edge 138 such that second region 134 has a generally circular configuration. However, other configurations are contemplated as being within the scope of the present invention. It is intended for second region 134 to spatially retain a selected fluid thereon, as hereinafter described. By way of example, it is contemplated for second region 134 to be hydrophilic. Alternatively, it can be appreciated that second region 134 may: 1) utilize various geometric configurations; 2) take the form of a well within upper surface 126 of first plate 124; or 3) include a wall extending around the periphery thereof to spatially retain the selected fluid thereon. For the reasons heretofore described, additional hydrophilic regions may be provided on upper surface 126 of first plate 124, without deviating from the scope of the present invention. The portion of upper surface 126 of first plate 124 outside of first and second regions 130 and 134, respectively, defines hydrophobic region 136.

Device 120 further includes an upper plate or slide 140 extending along a longitudinal axis generally perpendicular to upper surface 126 of first plate 124 and being defined by an upper surface 142, a generally convex lower surface 144 and an outer surface 146 therebetween. Outer surface 146 of slide 140 intersects lower surface 144 of slide 140 at generally circular edge 148. It can be appreciated that edge 148 can have other configurations without deviating from the scope of the present invention. Slide 140 further include hydrophobic tape 150 covering the entirety of lower surface 144 thereof and overlapping edge 148. Tape 150 renders lower surface 144 of slide 140 hydrophobic, for reasons hereinafter described. Slide 140 further includes a magnet receiving passageway 152 extending along the longitudinal axis of slide 140 from upper surface 142 towards lower surface 144. Passageway 152 terminates at end surface 154 which is in close proximity to lower surface 144 of slide 140. Passageway 152 is adapted for slidably receiving magnet 156 therein. It is intended for magnet 156 to be axially movable between a first position wherein magnet 156 is adjacent end surface 154 and a second position axially spaced from end surface 152, for reasons hereinafter described. Magnet 156 may be moved with passageway 152 between the first and second positions in any conventional manner such as by mechanical means, a vacuum, a magnetic force or the like.

In order to extract the targeted fraction from biological sample 36, droplet 160 of biological sample 36 is deposited on first region 130 in any conventional matter such as by a micropipette or like. In addition, droplet 162 of a desired reagent is deposited on second region 134. It is contemplated for the volumes of droplets 160 and 162 to be generally equal. Slide 140 is positioned such that tape 150 on lower surface 144 thereof is in close proximity to or makes contact with droplets 160 and 162 and such that magnet 156, in its first position, is axially aligned with first region 130 of upper surface 126 of first plate 124. Lower surface 144 of slide 140, and hence tape 150, is maintained a predetermined distance from upper surface 126 of first plate 124 such that droplets 160 and 162 maintain their generally cylindrical shapes and are not squashed, FIG. 8.

With slide 140 positioned as heretofore described, magnet 156 magnetically attracts fraction-bound solid phase substrate 38 such that fraction-bound solid phase substrate 38 are drawn toward lower surface 144 of slide 140. With first plate 124 remaining stationary, slide 140 is moved axially in a first direction, FIG. 9. As slide 140 is moved, magnet 156 retains fraction-bound solid phase substrate 38 against tape 150, and hence lower surface 144 of slide 140, thereby allowing fraction-bound solid phase substrate 38 to break the surface tension of droplet 160 when fraction-bound solid phase substrate 38 reach the outer periphery thereof. Slide 140 continues to be moved in the first direction such that magnet 156 is axially aligned with second region 134 of upper surface 126 of first plate 124, FIG. 10. Fraction-bound solid phase substrate 38 may be deposited in droplet 162 on second region 134 simply by moving magnet 156 axially away from end surface 154 toward upper surface 142 of slide 140. To assure that all of fraction-bound solid phase substrate 38 are retained in droplet 162, slide 140, and hence magnet 156, may be slid axially past droplet 162 prior to axially moving magnet 156 away from end surface 154. More specifically, the movement of first plate 124 and slide with respect to each other causes Couette flow within droplet 162 such that droplet 162 mixes within itself. In addition, the surface tension of the posterior end of droplet 162 pulls fraction-bound solid phase substrate 38 off hydrophobic tape 150 on lower surface 144 of slide 140.

It is further contemplated to provide a second magnet 166 orientated with the opposite polarity as magnet 156 at a location below second region 134 adjacent lower surface 128 of first plate 124. As such, upon release of fraction-bound solid phase substrate 38 into droplet 162, heretofore described, fraction-bound solid phase substrate 38 will have a strong affinity to second magnet 166. This, in turn, causes fraction-bound solid phase substrate 38 to switch polarity. As the magnetic force of second magnet 166 acts to attract fraction-bound solid phase substrate 38 toward upper surface 126 of first plate 124, magnet 156 acts as a repulsive force of opposite polarity thereby urging fraction-bound solid phase substrate 38 away from lower surface 144 of slide 140

It can be appreciated that the above description of device 120 is merely exemplary of the present invention. Various modifications to device 120 are possible without deviating from the scope of the present invention. By way of example, it is contemplated for first plate 124 to be axially moveable with respect to slide 140, such movement of first plate 124 (or a combination of movement of first plate 124 and slide 140) results in the droplets 160 and 162 aligning with magnet 156, for reasons heretofore described. It is further contemplated to provide additional (or fewer) hydrophilic regions on upper surface 126 of first plate 124 so as to allow a user to effectuate additional (or fewer) processing steps on fraction-bound solid phase substrate 38, e.g. additional washings of fraction-bound solid phase substrate 38. Further, upper surface 126 of first plate 124 may include an array of hydrophilic regions circumferentially spaced thereon and a corresponding array of slides 140. As a result, a plurality of extraction operations in accordance with the methodology of the present invention may be simultaneously conducted utilizing a single device 120. In such an arrangement, it is contemplated to provided a wall or fence about each "set" of hydrophilic regions so as to effectively isolate each "set" of hydrophilic regions from the other sets in the array, thereby preventing potential cross contamination between the sets Various modes of carrying out the invention are contemplated as being within the scope of the following claims particularly pointing out and distinctly claiming the subject matter, which is regarded as the invention.

We claim:

1. A method for isolating a target from a biological sample, the target being bound to a solid phase substrate to form a target-bound solid phase substrate, comprising the steps of:

providing the biological sample at a first region of an upper surface of a lower plate lying in a first plane and a fluid at a second region of the upper surface of the lower plate spaced from the first region;

positioning an upper plate lying in a second plane generally parallel to the first plane in spaced relation to the lower plate, the upper plate having a lower surface directed to the upper surface of the lower plate;

drawing the target-bound solid phase substrate toward the lower surface of the upper plate with a force;

retaining the target-bound solid phase substrate adjacent the lower surface of the upper plate with the force; and with the target-bound solid phase substrate retained adjacent the lower surface of the upper plate with the force, moving at least one of the lower plate along the first plane and the upper plate along the second plane from a first position wherein the target-bound solid phase substrate is received in the biological sample to a second position wherein the target-bound solid phase substrate communicates with the fluid at the second region of the upper surface of the lower plate and is isolated from the biological sample.

2. The method of claim 1 wherein the first region of the upper surface of the lower plate is hydrophilic.

3. The method of claim 1 wherein the upper surface of the lower plate includes a plurality of regions that are hydrophilic, the first region being one of the plurality of regions of the upper surface of the lower plate and the second region being one of the plurality of regions of the upper surface of the lower plate.

4. The method of claim 3 wherein the upper surface of the lower plate has portions outside of the plurality of regions, the portions of the upper surface of the lower plate outside the plurality of regions being hydrophobic.

5. The method of claim 1, wherein the lower surface of the upper plate is hydrophobic.

6. The method of claim 2 wherein the upper plate moves along a longitudinal axis between the first and second positions.

7. The method of claim 2 wherein the upper plate is rotatable between the first and second positions.

* * * * *